(12) United States Patent
Shikani et al.

(10) Patent No.: US 6,588,428 B2
(45) Date of Patent: Jul. 8, 2003

(54) SPEAKING VALVE FOR A TRACHEOSTOMY TUBE

(75) Inventors: Alan H. Shikani, Ruxton, MD (US); Joseph J. French, Joppatowne, MD (US)

(73) Assignee: Adam Spence Corp., Wall, NJ (US)

( * ) Notice: Subject to any disclaimer, the term of this patent is extended or adjusted under 35 U.S.C. 154(b) by 140 days.

(21) Appl. No.: 09/791,927

(22) Filed: Feb. 23, 2001

(65) Prior Publication Data

US 2002/0157674 A1 Oct. 31, 2002

(51) Int. Cl.$^7$ .......................... A61M 16/00; A62B 9/02; A62B 9/06
(52) U.S. Cl. .......................... 128/207.16; 128/207.14; 128/207.15
(58) Field of Search .................. 128/207.14, 207.15, 128/207.16, 207.17, 911, 912, DIG. 26

(56) References Cited

U.S. PATENT DOCUMENTS

| | | | |
|---|---|---|---|
| 3,066,674 A | 12/1962 | Capra | ........................ 128/351 |
| 3,924,637 A | 12/1975 | Swanson | ..................... 128/351 |
| 5,048,518 A | 9/1991 | Eliachar et al. | ........ 128/207.14 |
| 5,433,747 A * | 7/1995 | Grundei | ........................ 623/9 |
| 5,505,198 A | 4/1996 | Siebens et al. | ........ 128/207.16 |
| 5,935,165 A * | 8/1999 | Schouwenburg | ............... 623/9 |

FOREIGN PATENT DOCUMENTS

| | | |
|---|---|---|
| DE | 3436.777 A | 4/1985 |
| GB | 1 217 554 | 4/1968 |

OTHER PUBLICATIONS

"Otolaryngology–Head and Neck Sugery", pp. 102–107, Jul. 2000, "New Unidirectional Airflow Ball Tracheostomy Speaking Valve", Shikani, French and Siebens.

* cited by examiner

Primary Examiner—Weilun Lo
Assistant Examiner—Darwin P. Erezo
(74) Attorney, Agent, or Firm—Armstrong, Westerman & Hattori, LLP

(57) ABSTRACT

A speaking valve for a tracheostomy tube which is disposed in the first end of the tube protruding from the throat of the patient. The valve has guiding ribs and a retainer to retain a ball within the end of the tube. The flow of air around the ball is unrestricted to reduce the force required to move the ball when the patient inhales and exhales. A spherical chamber is formed in which the ball is disposed. The tracheostomy tube with the valve in the first end presents a low profile.

4 Claims, 7 Drawing Sheets

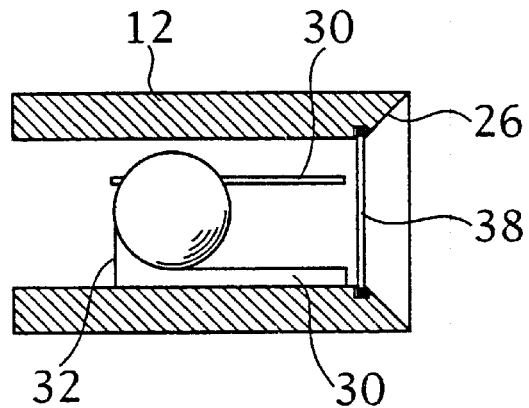
Fig 20
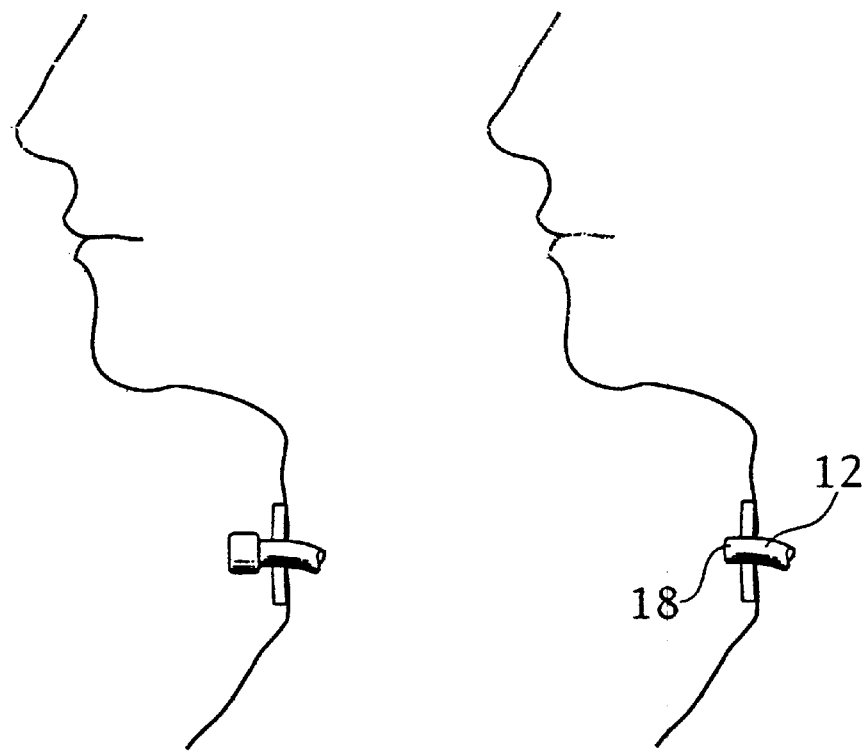
Fig 21
PRIOR ART
Fig 22

SPEAKING VALVE FOR A TRACHEOSTOMY TUBE

FIELD OF THE INVENTION

The present invention is directed to a valve for a tracheostomy tube and, more specifically, to a speaking valve having substantially unrestricted linear air flow through the valve.

BACKGROUND ART

Patients who have experienced tracheostomy and the insertion of a tracheostomy tube frequently have difficulties in their perceptual speech because the exhaled air does not produce sufficient vibratory movement of the vocal cords. This is very disturbing to the patient, the patient's family and healthcare personnel. The problem has been recognized for many years and the applicants are aware of efforts to provide a tracheostomy tube with improved speech characteristics. Many of these tubes have controlled air leaks, additional cuffs, pneumatic vibrators, springs, diaphragms and valve flaps. Other tubes have a valve with a moving ball such as disclosed in the following U.S. patents.

| Patent No. | Inventor(s)     | Issued          |
|------------|-----------------|-----------------|
| 3,066,674  | Capra           | Dec. 04, 1962   |
| 3,924,637  | Swanson         | Dec. 09, 1975   |
| 5,048,518  | Eliachar et al  | Sept. 17, 1991  |
| 5,505,198  | Siebens et al   | April 09, 1996  |

UK Patent No. 1 217 554, Dec. 31, 1970 and German Patent No. DE 3436-777-A, Apr. 25, 1985 also disclose a moving ball speech valve. A moving ball speaking valve is further disclosed in "Otolaryngology-Head and Neck Surgery", pages 103–107, Jul. 2000, "New Unidirectional Airflow Ball Tracheostomy Speaking Valve", Shikani, French and Siebens.

One major factor which has not received much attention in the design and fabrication of tracheostomy tubes is the flow of air within the cannula and the valve. An interface occurs at the end of the cannula exteriorly of the patient. The two dimensional orifice, having no length, restricts the free flow of room air into the cannula. The pressure drop across the orifice is the pressure necessary for a given flow rate through the cannula. The conventional orifice is not efficient because only the air in the immediate vicinity of the opening is drawn into the cannula. A mismatch occurs between the room air and the cannula and there is a further increase in the pressure required for a given flow rate. Further, any discontinuity inside the cannula can be viewed as an orifice which adds to the pressure necessary for the flow of air through the cannula. The discontinuity may be irregularities on the inner wall. When a flapper valve is connected to the end of the cannula the valve housing has a linear effect on the impedance but the flap, by its spring-like nature, adds a non-linear increase to the impedance of the system. This increase of impedance to inhalation is most noticeable at low flow rates. This is also true with disk valves. This effect can be greatly reduced by making the flap or disk larger resulting in an increase in the housing size. This would make the valve too unwieldy to be practical. The ball valve by its nature is more compact since its outside diameter can be much smaller than the flapper or disk valves. The problem with the ball valve is that, in its simplest form, at least two additional interfaces are created which add to the system impedance on inspiration. Unlike the flapper or disk valves this effect can be minimized without increasing the outside diameter of the valve. The present invention is directed to solving this problem.

Despite the efforts to date, there is still a problem to provide a tracheostomy tube with good speech characteristics.

SUMMARY OF THE INVENTION

It is an object of the present invention to provide a speaking valve for a tracheostomy tube which offers reduced air resistance and enhances clarity and ease of speech by the patient.

It is a further object of the present invention to provide a tracheostomy tube with a speaking valve which has an unextended profile and has minimal visibility.

In accordance with the teachings of the present invention, there is disclosed a valve in combination with a tracheostomy tube, the tube having a first open end adapted to protrude from the throat of a patient. A cylindrical body having an outer diameter is snugly received within the first end of the tracheostomy tube. A retaining means is disposed within the cylindrical body distal from the first open end of the tube. A ball is disposed between the first open end of the tube and the retaining means. Seating means for the ball is disposed at the first open end of the tube. Guiding means are formed within the tracheostomy tube to maintain the ball substantially centered within the tracheostomy tube wherein air flow about the ball is unrestricted. When the patient exhales, due to the unrestricted air flow, minimum force is required to move the ball against the seating means to seal the opening in the first end of the tube and prevent exhaled air from exiting the tracheostomy tube forcing air through the larynx, and when the patient inhales, the ball is moved away from the seating means in the first end of the tube and retained by the retaining means wherein air enters the tracheostomy tube.

In further accordance with the teachings of the present invention, there is disclosed a hollow tracheostomy tube adapted to be received in the throat of a patient. The tracheostomy tube has a first end protruding from the neck of the patient and a second end extending into the trachea of the patient below the larynx. The improvement is a speaking valve having a cylindrical body having a first end. A flange is formed circumferentially about the first end of the body such that the cylindrical body is received in the first end of the tracheostomy tube with a friction fit. The flange on the body holds the valve at the first end of the body. A retaining means is disposed within the body distal from the flange. An opening is formed in the flange. A ball is disposed between the opening and the retaining means. A plurality of circumferentially spaced-apart ribs are formed in the body of the speaking valve, each rib being approximately perpendicular to the flange. The ball is guided by the ribs. The ball is substantially centered within the tracheostomy tube wherein linear air flow around the ball is unrestricted. The air moves at constant velocity when the patient inhales and exhales, the ball moving between the opening in the flange and the retaining means.

In still further accordance with the teachings of the present invention, there is disclosed a hollow tracheostomy tube adapted to be received in the throat of a patient. The tracheostomy tube has a first end having an opening and protruding from the neck of the patient and a second end extending into the trachea of the patient below the larynx.

The improvement is a retaining means disposed within the tracheostomy tube near the first end of the tube. A ball is disposed on the plurality of circumferentially spaced-apart ribs and guided on the ribs. Air flow around the ball is unrestricted In yet further accordance with the teachings of the present invention, there is disclosed a tracheostomy tube including a cannula provided with a speaking valve assembly having a floating ball therein. The ball is guided for limited longitudinal movement within the speaking valve assembly. The air flow around the ball is at a substantial constant velocity, thereby substantially reducing the force required to be exerted by the patient to close the speaking valve assembly during exhalation, and thereby quickly activating the patient's vocal cords for clearer and easier patient speech.

These and other objects of the present invention will become apparent from a reading of the following specification taken in conjunction with the enclosed drawings.

BRIEF DESCRIPTION OF THE DRAWINGS

FIG. 17 shows the ball in at a rest position within the tracheostomy tube.

FIG. 18 shows the ball held at the retaining means during inhalation with air flow around the ball.

FIG. 19 shows the ball seated in the flange opening and air passing into the larynx during expiration.

FIG. 20 is a longitudinal-sectional view showing the ball, guiding means and retaining means disposed within the first end of the cannula.

FIG. 21 is a diagram of a prior art tracheostomy tube with a speaking valve attached to the end of the tracheostomy tube exteriorly of the patient's neck.

FIG. 22 is a diagram of the present invention in the exterior end of a tracheostomy tube providing an unextended profile.

DESCRIPTION OF THE PREFERRED EMBODIMENTS

Figure 1:
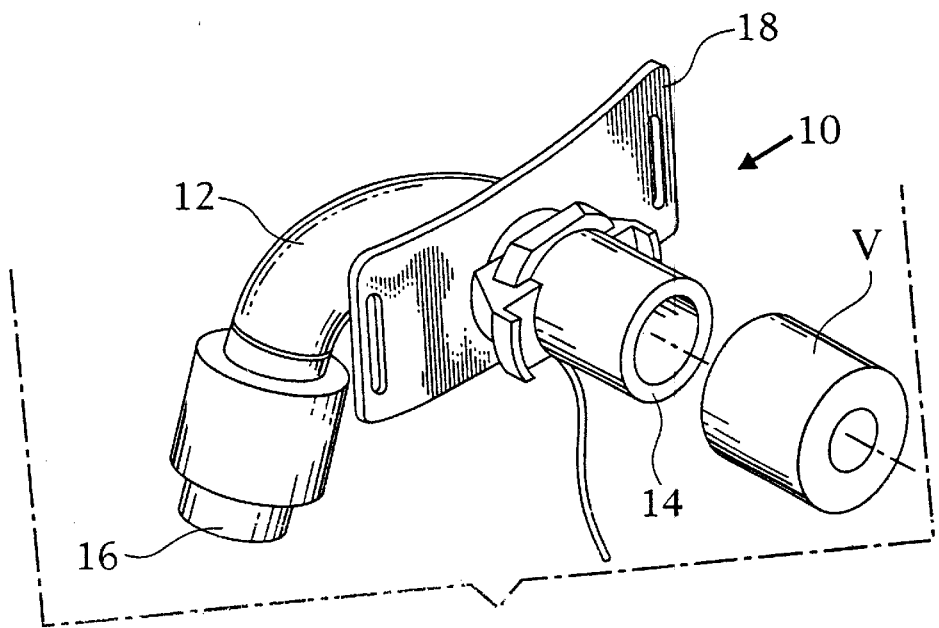
FIG. 1 is the prior art of a typical tracheostomy tube with a speaking valve removably disposed thereon.

Referring now to FIGS. 1–16, a tracheostomy tube 10 is a cannula 12 having an open first end 14 which extends outwardly from the throat of a patient and a second end 16 which is surgically inserted into the trachea of the patient. The second end 16 is directed downwardly toward the lungs of the patient with the tracheostomy tube 10 being below the larynx. A neck plate 18 is connected to the outside of the cannula 12 and is disposed on the outside of the patient's throat to stabilize the cannula 12 within the surgical opening in the throat. In the prior art (FIG. 1) a speaking valve V is fitted over the standard 15 mm cannula and further extends the tracheostomy tube from the throat of the patient.

Figure 2:
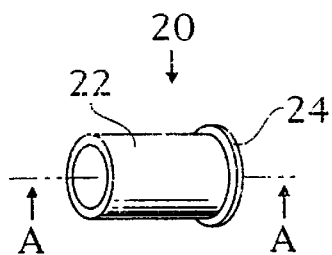
FIG. 2 is a perspective view of the valve of the present invention. The typical tracheostomy tube is omitted for ease of illustration.
Figure 3:
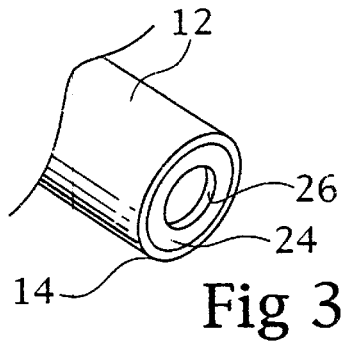
FIG. 3 is a perspective view of a tracheostomy tube with the valve of the present invention received in the tube.
Figure 4:
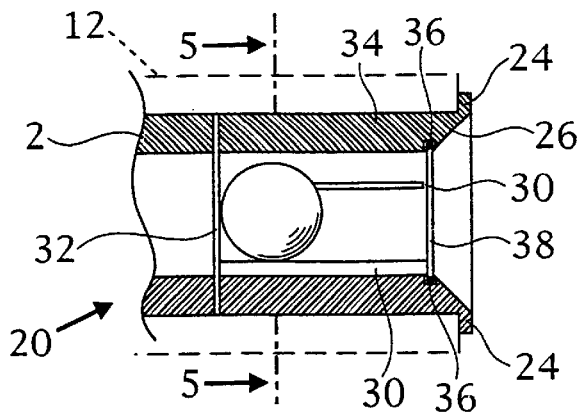
FIG. 4 is a longitudinal-section view taken across the lines A—A of FIG. 2 showing one embodiment. The tracheostomy tube is shown in broken lines.
Figure 5:
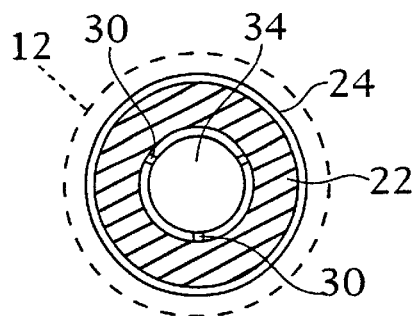
FIG. 5 is a cross-section view thereof taken across the lines 5—5 of FIG. 4.

FIG. 2 shows the valve 20 of the present invention. FIG. 3 shows the valve 20 inserted into the open first end 14 of the cannula 12. The valve 20 has a hollow cylindrical body 22 with an outer diameter which is snugly received (with a friction fit) within the open first end 14 of the tracheostomy tube 10. A flange 24 is formed on a first end of the cylindrical body 22. When the body 22 is disposed in the first end 14 of the cannula 12, the flange 24 abuts the cannula and retains the body 22 at the first end 14 of the cannula 12 with a low profile. An opening 26 is formed centrally in the flange 24. Preferably, the opening 26 is a counterbore which is tapered to have a decreasing diameter from the outer end of the body 22 in a funnel shape. This tapered opening 26 efficiently funnels outside air into the first end 14 of the tracheostomy tube 10 greatly reducing the pressure required for a given flow rate of air.

In a first embodiment (FIGS. 4–5) a plurality of guiding means 30 are formed within the cylindrical body 22. Preferably, the guiding means 30 are at least three circumferentially spaced-apart longitudinal ribs formed on the inner surface of the hollow cylindrical body 22. The guiding means (ribs 30) are very thin to have minimum effect on air flow through the body as explained above. A thickness of approximately 0.01 inches is preferred. Retaining means 32 are disposed within the cylindrical body 22 distal from the flange 24. The ribs or guiding means 30 have a length extending from the opening 26 to the retaining means 32. The retaining means 32 may be of various types as will be explained. In the first embodiment, the retaining means 32 is a pin through the body 22. A ball 34 is disposed within the body 22 between the flange 24 and the retaining means 32 and intermediate of the guiding means 30. The ball is substantially centered within the cylindrical body 22 and the tracheostomy tube 10. An annular groove 36 is formed within the body 22 adjoining the opening 26. A ring 38 is disposed in the annular groove 36 and serves as a seat for the ball 34 when the patient exhales. The ball 34 is seated in the seal 38 and exhaled air is prevented from passing through the tracheostomy tube but is forced up the trachea passing the larynx.

Figure 6:
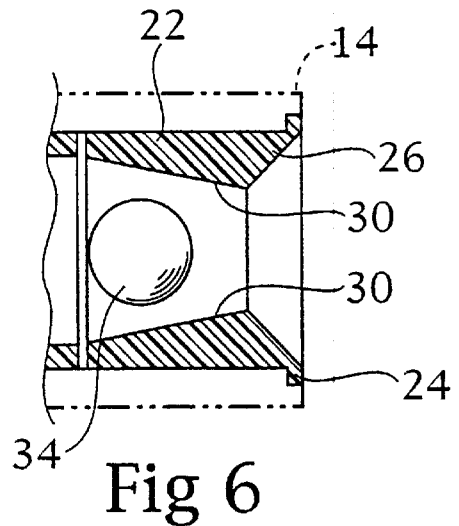
FIG. 6 is a longitudinal-section view taken across the lines A—A of FIG. 2 showing a second embodiment. The tracheostomy tube is shown in broken lines.

FIG. 6 shows a second embodiment of the body 22 in which the guiding means 30 are the walls of a frustoconical chamber formed within the body 22. When the patient exhales, the ball is moved toward the opening 26 and forms a seal with the guiding means 30. When the patient inhales, the ball moves away from the opening allowing air to enter the body 22. The ball 34 is retained in the body 22 by the pin through the body 22 which acts as the retaining means 32.

Figure 7:
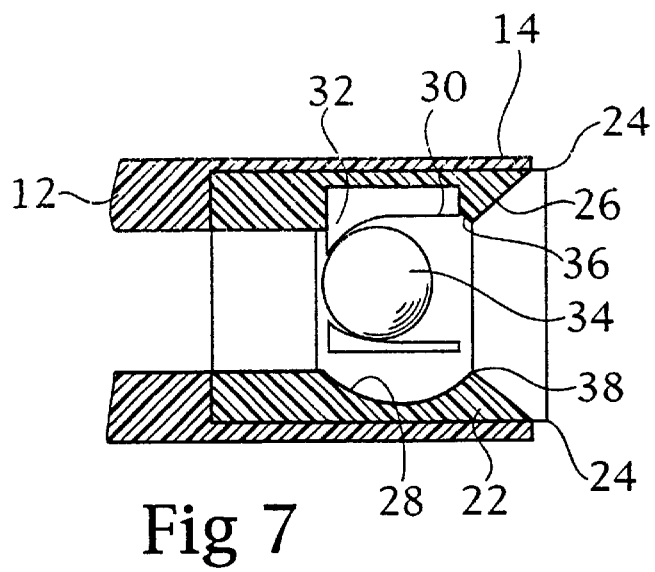
FIG. 7 is a longitudinal-section view taken across the lines A—A of FIG. 2 showing a third embodiment.
Figure 8:
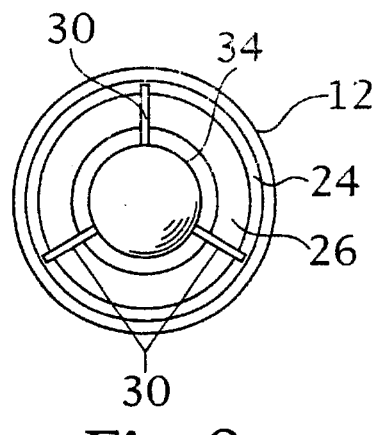
FIG. 8 is an end view of the valve of FIG. 7 received in the tracheostomy tube.
Figure 9:
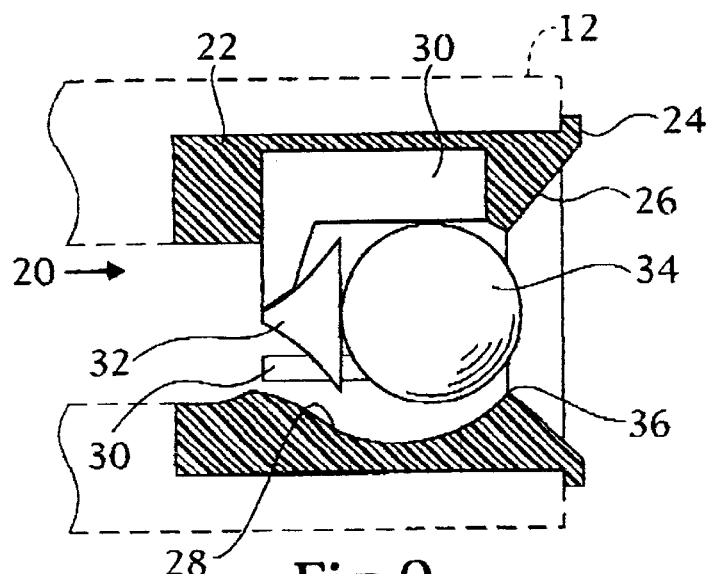
FIG. 9 is a longitudinal-section view taken across lines A—A of FIG. 2 showing a fourth embodiment.
Figure 10:
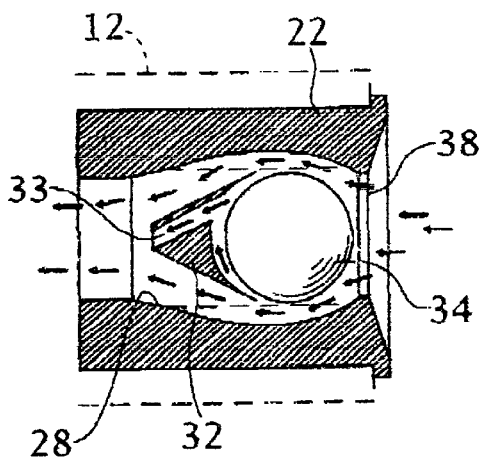
FIG. 10 is a corresponding view of FIG. 9 but showing air movement during inhalation, the guiding means not being shown
Figure 11:
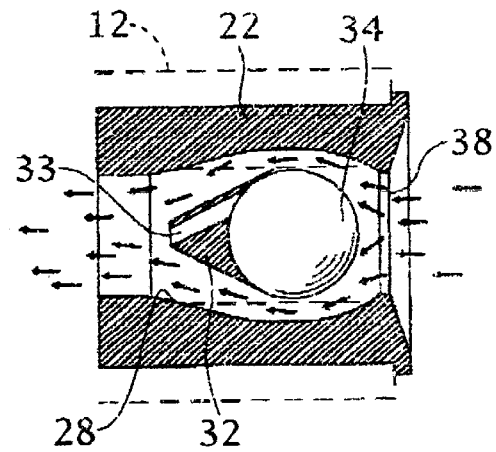
FIG. 11 is the view of FIG. 10 showing air movement when the ball is seated in the retaining means.
Figure 12:
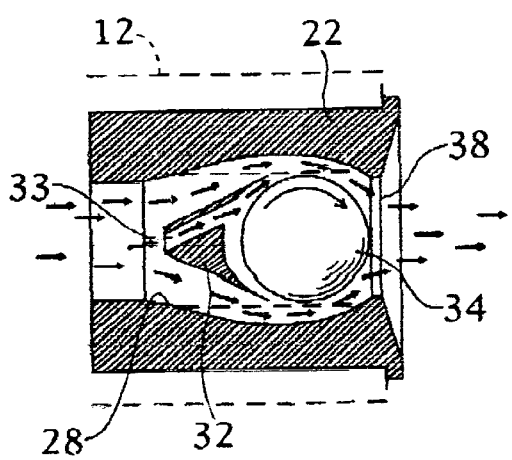
FIG. 12 is the view of FIG. 10 showing air movement during exhalation.
Figure 13:
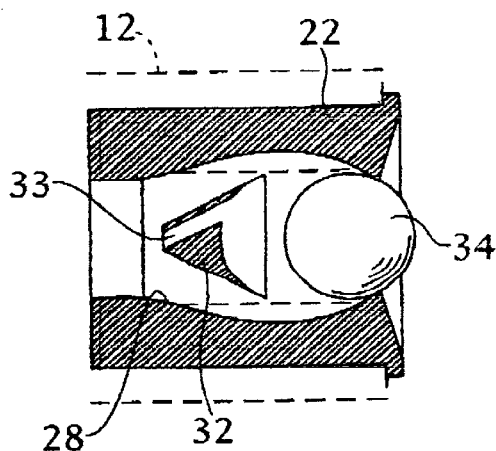
FIG. 13 is the view of FIG. 10 showing the ball seated in the seal such that there is no air movement.
Figure 14:
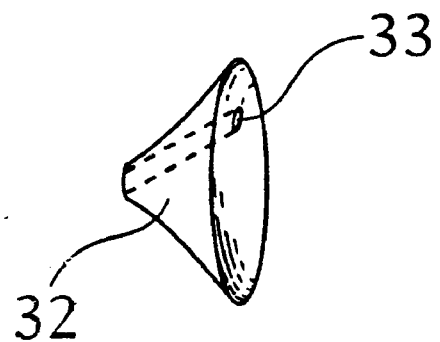
FIG. 14 is a perspective view of the retaining means of FIG. 9.
Figure 15:
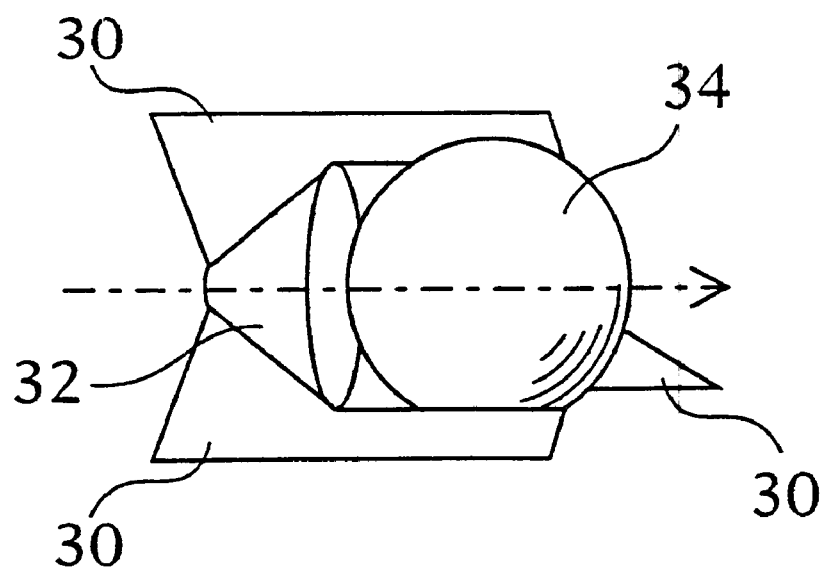
FIG. 15 is a perspective view of the funnel-shaped retaining means, the guiding means and the ball.

A third embodiment of the present invention is shown in FIGS. 7-8. An insert is removably received in the first end 14 of the cannula 12. The insert has a body 22 with a flange 24 which abuts the first end 14 of the cannula 12. The body 22 has a tapered opening 26 to funnel the air into the tracheostomy tube. A spherical chamber 28 is formed within the body 22 communicating with the opening 26. Guiding means 30 are formed within the body 22 across the spherical chamber 28. The ball 34 is disposed within the chamber 28 intermediate of the guiding means 30.

As shown in FIG. 7, the retaining means 32 is an inwardly curving end of the guiding means 30 distal from the flange 24. A seat 38 is formed at the juncture of the spherical chamber 28 and the tapered opening 26 wherein the ball 34 forms a seal when the patient exhales.

Figure 16:
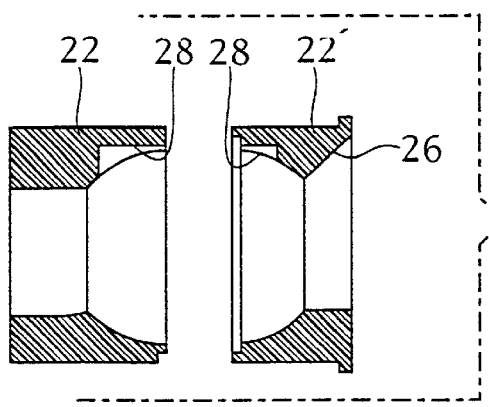
FIG. 16 is a cross-sectional view showing the body in two pieces.

In a fourth embodiment, as shown in FIGS. 9–15, the retaining means 32 is a funnel-shaped member disposed along an approximate center line through the tracheostomy tube. The body 22 may be formed of two pieces 22, 22' for ease of manufacture as shown in FIG. 16.

Figure 17:
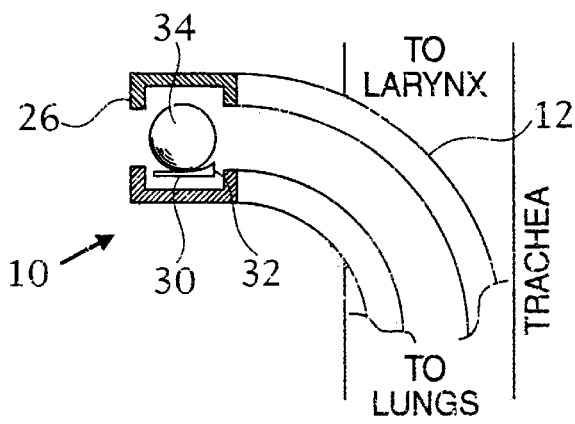
FIGS. 17–19 is a sequence of diagrams showing the operation of the present invention.
Figure 18:
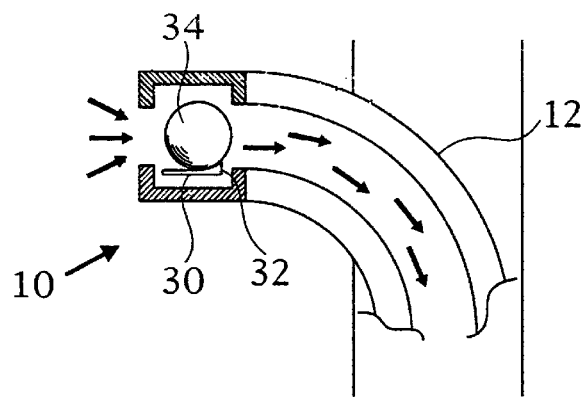
Figure 19:
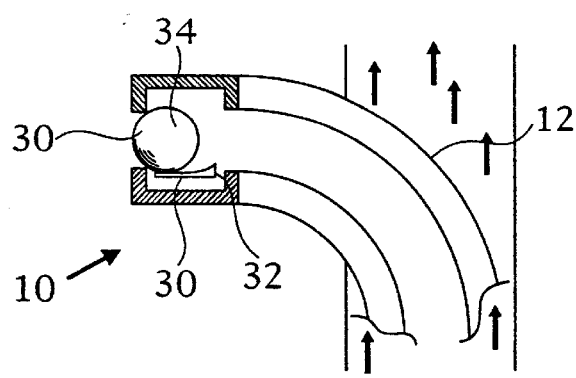

FIGS. 17–19 show the operation of the present invention. At rest (FIG. 17) the ball 34 is intermediate of the guiding means 30 between the opening 26 in the flange and the retaining means 32. When the patient inhales (FIG. 18), the air incoming through the opening 26 moves the ball 34 against the retaining means and air flows in an unrestricted manner into the lungs of the patient. When the patient exhales (FIG. 19), minimal force of the initial breath pushes the ball 34 against a seat 36 formed on the inner face of the opening 26, the opening 26 due to the configuration of the present invention. The majority of the exhaled air passes the tracheostomy tube and enters the larynx improving the quality of speech of the patient.

Referring back to FIGS. 9–15, the retaining means 32 is aerodynamically configured to prevent turbulence at the ball 34 distal from the flange. The cross-sectional area of the seat 38 must be no smaller than that of the cannula. The ball 32 must be no larger than that required to produce a good seal with the seat 38 when the patient exhales. The inner surface of the chamber 28 is designed to present a constant cross-sectional area between the inner surface of the chamber 28 and the retaining means 32 to the flow of incoming air. This cross-sectional area is equal to that of the cannula. It is the area which the air encounters in flowing through the valve and is substantially perpendicular to the surface of the ball and retaining means. This constant cross-sectional area avoids changes in pressure which are required to move the air through the tracheostomy tube both on inhalation and exhalation. The concave inner surface of the retaining means 32 cooperates with the ball 34 and, when fully retained, presents a substantially uninterrupted surface for the unrestricted flow of incoming air completely around the circumference of the ball 34. The absolute air velocity is constant from the seat 38 through the cannula.

It is also preferred to have an air tunnel 33 formed in the retaining means 32. During inhalation, air flows through the air tunnel 33 until the ball 34 is seated in the retaining means 32. If the air tunnel 32 were not present, there is a possibility that a cushion of air would remain in the retaining means 32 and the ball 34 would not be seated. For exhalation, air from the patient's lungs is directed around the ball 34 and also through the air tunnel 33. Thus, the air tunnel 33 assists in exhalation by directing air against the ball 34 at an angle, causing the ball 34 to spin, thereby accelerating the closure of the valve. Maximum pressure is desired to move the ball 34 to close the valve as fast as possible.

As shown in FIG. 20 the present invention may be formed within the first end 14 of the cannula 12 and not be a separate removable insert. The opening 26 is tapered to funnel air into the first end 14 of the tracheostomy tube 10. Guiding means 30 are formed within the first end 12 of the tracheostomy tube. The guiding means 30 shown in FIG. 20 have an inwardly curving end distal from the opening 26 to serve as a retaining means 32 but any retaining means may be used. FIG. 20 is for illustration and is not limiting. The ball 34 is disposed on the guiding means 30. A seal 38 is formed at the juncture of the tapered opening 26 and the inner diameter of the first end 14 of the cannula 12 wherein the ball 34 is seated against the seal 38 when the patient exhales. The ball 34 moves on the guiding means 30 between the retaining means 32 and the seal 38. In this embodiment, there is no insert within the first end 14 of the tracheostomy tube 10.

The prior art disclosed a removable speech valve which is received on the exterior end of the tracheostomy tube as shown in FIG. 21. The valve extends outwardly so that it is bothersome to the patient and is easily noticeable by the public. FIG. 22 shows the tracheostomy tube having the speech valve of the present invention within the exterior end of the tracheostomy tube so that the profile is unextended. The patient is more comfortable and the tube is less noticeable.

Figure 23:
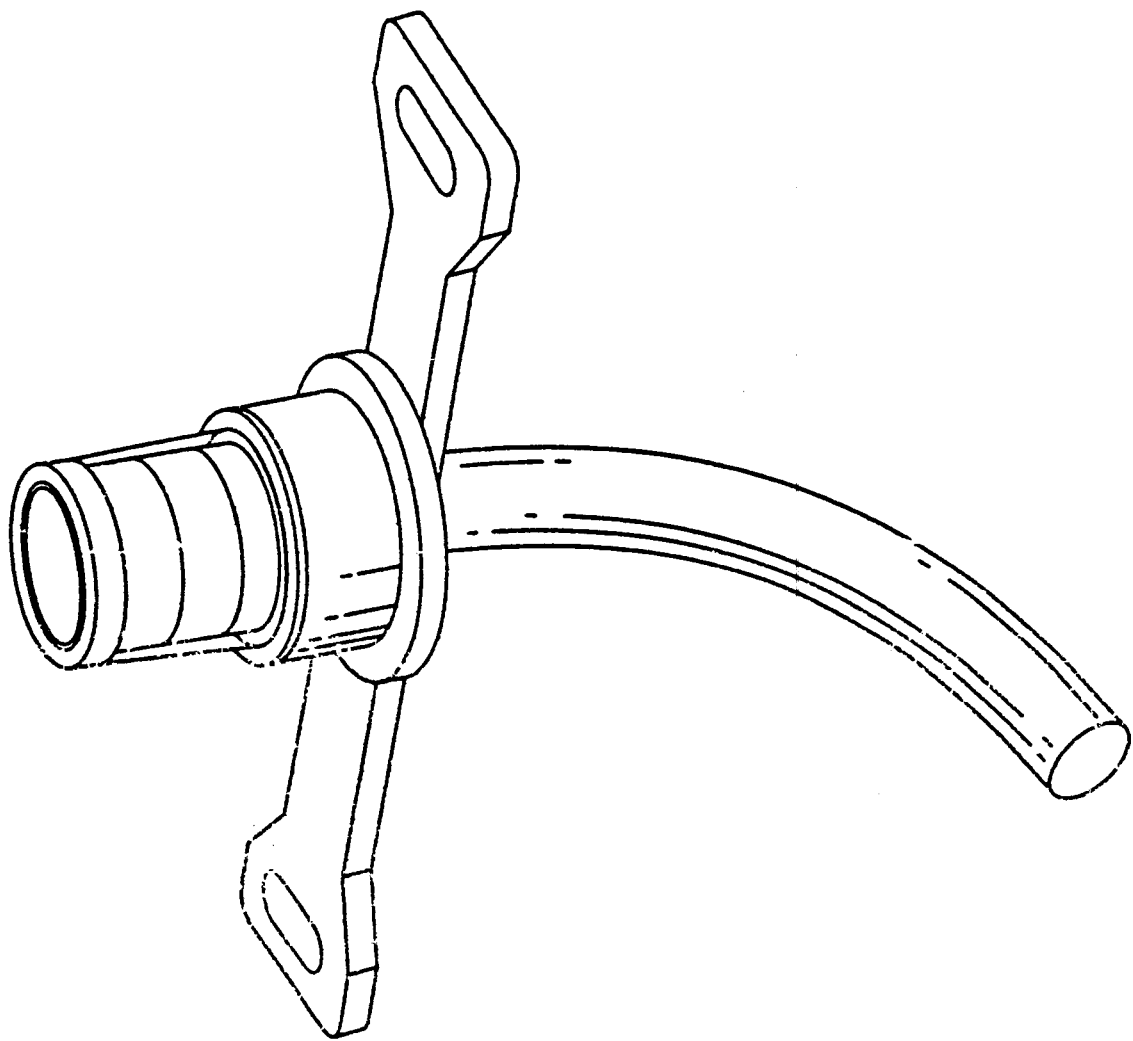
FIG. 23 is a perspective view showing a commercially available tracheostomy tube.

The speaking valve of the present invention can be received in the tracheostomy tube inlet of most commercially available devices. FIG. 23 shows the adult tracheostomy tube cuffless. Ref. 00A160 made by BIVONA® Medical Technologies, Gary Ind. Although not shown, the speaking valve of the present invention can also be used with tracheostomy tubes marketed by, but not limited to, the following:

| Company Name | City, State | Product Trade Name |
| --- | --- | --- |
| Mallinckrodt Medical | St. Louis, MO | Shiley ® |
| Bivona Medical Technologies | Gary, Indiana | TTS Tracheostomy Tube |
| SIMS Inc. | Keene, NH | Per-Fit ™ Trachea Tube |
| | | D.I.C. ® Trachea tube |
| | | Blue Line ® |
| | | Portex ® |
| Pilling Surgical | Ft. Washington, PA | Jackson Trachea Tubes |
| Technical Products Inc. | Decatur, GA | Hood Medical |
| Dale Medical Product Inc. | Plainsville, MI | Dale Trachea Tube Holder |

A ball valve in the cannula to control inspiration and expiration of air must consider flow rates through the tube and the valve. Anytime there is a transition from a larger cross-sectional area to a smaller cross-sectional area, an interface is created which changes the opposition presented to air flow. Ideally, the cross-sectional area presented to the movement of air should be constant within the cannula. In order to approach a constant cross-sectional area, a spherical chamber within the cannula is suggested to house a ball check valve. The difference between the cross-sectional area of the chamber and that of the ball is equal to the cross-sectional area of the cannula so that there are no transitions from larger to smaller cross-sectional areas and, hence, air flow is at a constant velocity. As a consequence, the force required to inhale and exhale is reduced and there is reduced burden on the patient. A further consequence is that the speech valve in the cannula closes more rapidly on inhalation due to the reduced force required and the vocal cords are activated almost immediately when the patient speaks. This overcomes the problems with the prior art in which speech is distorted because part of the force of the patient's breath is required to close the speech valve before the remainder of the breath activates the vocal cords.

Obviously, many modifications may be made without departing from the basic spirit of the present invention. Accordingly, it will be appreciated by those skilled in the art that within the scope of the appended claims, the invention may be practiced other than has been specifically described herein.

What is claimed is:

1. In a hollow tracheostomy tube adapted to be received in the throat of a patient, the tracheostomy tube having a first end protruding from the neck of the patient and a second end extending into the trachea of the patient below the larynx, the improvement comprising:

a speaking valve having a cylindrical body having a first end, a flange formed circumferentially about the first end of the cylindrical body such that the cylindrical body is received in the first end of the tracheostomy tube with a friction fit, the flange in the cylindrical body holding the speaking valve at the first end of the cylindrical body, a means for retaining a ball disposed within the cylindrical body distal from the flange, an opening formed in the flange, said ball being disposed between the opening and the means for retaining the ball, a plurality of circumferentially spaced-apart ribs formed in the body of the speaking valve, each rib being approximately perpendicular to the flange, the ball being guided by the ribs, the ball being substantially centered within the tracheostomy tube wherein the air flow around the ball is unrestricted and the air moves at constant velocity when the patient inhales and exhales, the ball moving between the opening in the flange and the means for retaining the ball.

2. In a hollow tracheostomy tube adapted to be received in the throat of a patient, the tracheostomy tube having a first end having an opening and protruding from the neck of the patient and a second end extending into the trachea of the patient below the larynx, the improvement comprising:

a means for retaining a ball disposed within the tracheostomy tube near the first end of the tube, a plurality of circumferentially spaced-apart ribs formed in the tracheostomy tube near the first end of the tube, the ribs each having a length extending from the opening in the tracheostomy tube to the means for retaining the ball, said ball being disposed on the ribs and guided on the ribs wherein the ball is substantially centered along a center line of the tracheostomy tube, wherein air flow around the ball is unrestricted and the air moves at a constant velocity when the patient inhales and exhales, the ball moving between the opening in the first end of the tracheostomy tube and the means for retaining the ball.

3. The tracheostomy tube of claim 2, wherein the ball is disposed in a cylindrical chamber within the tracheostomy tube.

4. In a patient's tracheostomy tube having a ball check valve, wherein the valve has a valve body with openings at either end thereof, and wherein the ball is free to move randomly and travels within the valve body and between the respective openings therein, such that the ball does not always seal off the respective openings, the improvement which comprises a ball centered between circumferentially-spaced longitudinal ribs within the valve body, such that the ball is restricted to longitudinal movement within the valve body and cannot move randomly therein, the valve body having a restrictive opening at one end thereof distal from the patient, the distal opening having a valve seat such that the ball closes off the opening when the patient exhales, and the valve body being substantially free of any restriction at its other end nearer to the patient, such that there is substantially no restriction to the airflow when the patient inhales, and a transverse pin mounted at the other end of the valve body to retain the ball within the valve body.

* * * * *